United States Patent [19]

Lupica

[11] 4,066,407

[45] Jan. 3, 1978

[54] BODY FLUID TESTING SYSTEM AND PROCESS

[76] Inventor: Vincent Lupica, 2621 Palisade Ave., Riverdale, N.Y. 10463

[21] Appl. No.: 751,108

[22] Filed: Dec. 16, 1976

[51] Int. Cl.² ........................ G01N 33/16; G01N 1/18

[52] U.S. Cl. ................................ 23/230 B; 23/253 R; 23/259; 73/425.4 P

[58] Field of Search ................. 23/230 B, 253 R, 259, 23/292; 141/130; 73/425.4 P; 233/26

[56] References Cited

U.S. PATENT DOCUMENTS

| | | | |
|---|---|---|---|
| 3,475,127 | 10/1969 | Gilford | 23/259 X |
| 3,713,780 | 1/1973 | Shapiro | 23/259 |
| 3,715,189 | 2/1973 | Nighohossian et al. | 23/259 |
| 3,859,051 | 1/1975 | Natelson | 23/259 |
| 3,938,957 | 2/1976 | Lanier et al. | 73/425.4 P |
| 3,992,150 | 11/1976 | Retzer | 23/259 |

*Primary Examiner*—R.E. Serwin
*Attorney, Agent, or Firm*—Eliot S. Gerber

[57] ABSTRACT

A laboratory mixing apparatus for the testing of blood or other liquids includes a prescored capillary pipette to accurately measure the fluid, a centrifuge and a pipette breaking device. The pipette is secured to a squeeze bulb which ejects the fluid, after being centrifuged, into the top cell of a multi-celled container. The container is positioned in the mixing apparatus and automatically, in selected timed sequence, if needed, warmed and agitated and the membrane between cells is automatically ruptured.

4 Claims, 10 Drawing Figures

BODY FLUID TESTING SYSTEM AND PROCESS

BACKGROUND OF THE INVENTION

In recent years there has occurred a vast increase in the amount and complexity of biomedical testing. To perform each test manually may be time consuming and expensive. Consequently, many physicians send body fluid samples, such as blood samples, to central laboratories for testing. However, the transportation of the samples to the central laboratory may not be convenient and the testing by the central laboratory may involve unnecessary expense.

The testing apparatus designed for central testing laboratories is generally complex and expensive, costing many thousands of dollars. Such machines are not suitable for use in physicians' offices, where the tests may be performed by relatively untrained personnel.

There is an increased need for a semi-automated system to analyze blood and other biological fluids. The requirements of such a system are that (a) it must be as automatic as possible, with as few as possible manual operations to be carried out by the technician; (b) it must be self-contained, both to increase sample sterility and to eliminate possible sample confusion; and (c) it must be sufficiently compact and inexpensive to be within the financial range of the small medical practitioner, and suited for his uses.

OBJECTIVES AND FEATURES OF THE INVENTION

It is an objective of the present invention to provide a laboratory mixing apparatus for the testing of blood, which apparatus is sufficiently low in cost and simple in operation so that it may be utilized by a physician or his technician in his own office.

It is a further objective of the present invention to provide a laboratory mixing apparatus for the testing of blood, which apparatus will provide a set of accurate and reliable test results.

It is a further objective of the present invention to provide a laboratory mixing apparatus for the testing of blood, which apparatus will operate semi-automatically and, after setting by the operator, without further operator attention.

It is a further objective of the present invention to provide a laboratory mixing apparatus for the testing of blood, which apparatus is adapted to utilize multicell containers in which each cell contains an accurate and sterile stored amount of chemical reagent.

It is a further objective of the present invention to provide a laboratory mixing apparatus for the testing of blood, which apparatus is adapted to perform a wide variety of blood chemistry tests, and other tests, which require various steps and times of heating, agitation, resting and centrifuging.

It is a further objective of the present invention to provide a laboratory mixing apparatus for the testing of blood, which apparatus includes a capillary pipette system for obtaining an accurate amount of blood, or other fluid, to be tested.

It is a feature of the present invention to provide a mixing apparatus for the automatic testing of body fluids, such as blood. The mixing apparatus includes an accurately prescored capillary pipette for drawing off body fluids. The pipette, after being filled with body fluid, centrifuged, and broken along the scoring line, has an accurate and predetermined volume of fluid retained in its upper portion. Means for controlling the ejection of fluid from said pipette is attached to the pipette. The apparatus further includes at least one multicelled liquid-impermeable container, for example, of plastic resin, having individual cells and a liquid-impermeable membrane between the cells. The apparatus has cell holding means, means for rupturing the membrane, motor means for moving the rupturing means to rupture the membrane, means for agitating and mixing solutions in the held cells, means for regulating the temperature of the container, means for accurately and reproducibly breaking said pipette along the scoring line, and means for centrifuging the contents of said pipette. A timing mechanism is used for regulating each of the rupturing motor, agitator and temperature regulation means.

It is a further feature of the present invention to provide a novel process for performing tests upon body fluids, such as blood, comprising the steps in sequence of collecting the body fluid in an accurately prescored capillary micropipette having opposed open ends; stopping an end of the pipette; centrifuging the pipette; breaking off the pipette at the score line to yield an accurate and predetermined volume of fluid retained in the pipette above its score line; transferring the retained fluid to the uppermost cell of a multicelled stacked container having rupturable liquid-impermeable membranes; agitating the contents of the container; rupturing the membrane between the uppermost cell and the next cell, thus causing the solution in the first cell to mix with the solution in the next cell; agitating the resulting mixture, and performing a test on the resulting solution.

BRIEF DESCRIPTION OF THE DRAWINGS

Other objectives and features of the present invention will be apparent from the following detailed description of the invention, taken in conjunction with the accompanying drawings, that description providing the best presently known mode of practicing the invention.

In the drawings.

DETAILED DESCRIPTION OF THE INVENTION

The multi-celled liquid impermeable container of the present invention consists of a plurality of individual cells separated by liquid-impermeable membranes. The cells are detachable from each other. The cells and the membranes are preferably made from injection-molded plastic resin such as nylon or polyethylene. The cells are removably attachable to each other to form the container by means of, for example, screw threads or snap-grooves. The entire container may be covered with a full-length protective cover, which is an overscabbard. Chemical test reagents, which are accurately measured and mixed, are stored within each cell, that is, the cells are shipped from the factory to the users with each cell containing a pre-measured and pre-mixed test reagent 9.

Figure 1:
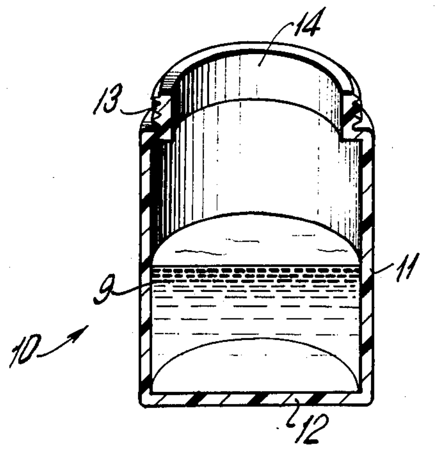
FIG. 1 is a perspective view, and a cross-sectional view, of the bottom-most cell of the container, the view showing the cell as if it had been cut in half along a vertical plane.

As shown in FIG. 1, the bottom cell 10 consists of a tubular portion 11 which is sealed at its end by an integral flat bottom portion 12 and has a top neck portion 13 having external screw threads. The hollow neck portion 13 has about ¾ the diameter of the tubular section and is designed to be attached to consecutive cells.

Figure 2:
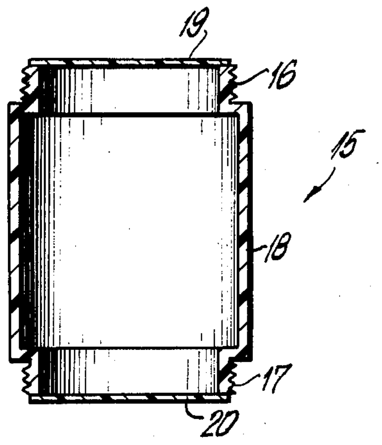
FIG. 2 is a cross-sectional view of an intermediate cell of the container.

The cells which attach to the bottom cell 10 may be of several embodiments. In the preferred embodiment, as shown in FIG. 2, each of these cells 15 is a hollow tubular cylinder 18 with ends tapered to form respectively top and bottom portions 16, 17 of the same diameter as the neck portion 13 of the bottom cell 10. Each of its two opposed neck portions 16, 17 has external screw-threads. Each of the neck portions 16, 17 may be sealed with a respective thin plastic membrane 19, 20 if the plastic ring 21 of FIG. 3, having an integral membrane, is not utilized. Alternatively to the screw threads, a snap-groove may be used for the attachment of the protective cover and the bottom cell. The top-most cell of the container may have, as its cover, a snap-off cap (not shown) in place of a membrane to permit the technician to readily remove the cap and expose the test reagent within the cell.

Figure 3:
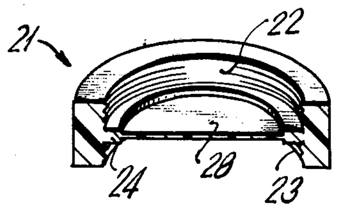
FIG. 3 is a combined perspective view, and in cross-section, of a joining ring showing one-half of the ring as if cut along a vertical plane.

Successive cells are connected by means of a molded plastic ring 21, FIG. 3. The ring 21 has a set of internal screw threads on the inside of the ring, such that the end of one connecting cell or a bottom cell screws into one end of the ring 22 and the neck portion of another cell screws into the other end 23 of the ring 21. Both cells are stopped by an internal bead 24 so as to form an air-tight, water-tight and sterile succession of cell-ring-cell. The plastic ring 21 contains a thin plastic membrane 28 as an extension of the bead 24. The ring may use snap grooves which would cooperate with beads on the cells, as an alternative to the screw threads. Alternatively, the plastic membrane 23 may be omitted (not shown) and the separate membranes 19, 20 used on the ends of each cell, as shown in FIG. 2.

Figure 4:
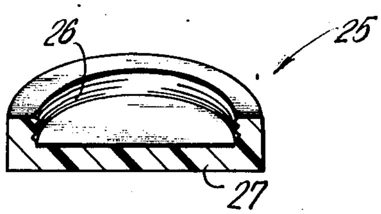
FIG. 4 is a view, similar to that of FIG. 3, but of a bottom member of the container.

An alternative embodiment of this array makes no distinction between bottom cells and connecting cells. All are shaped substantially as illustrated in FIG. 2 and utilize connecting rings as in FIG. 3. In order to facilitate the placing of the bottom-most cell into the mixer apparatus, a molded plastic adapter 25, FIG. 4, is used. Its cavity is the reverse mold of the neck portion of the cell and it has internal screw threads 26 and a bottom portion 27 which is flat. It is attached to the neck portion of the cell by means of the screw threads 26.

Figure 5:
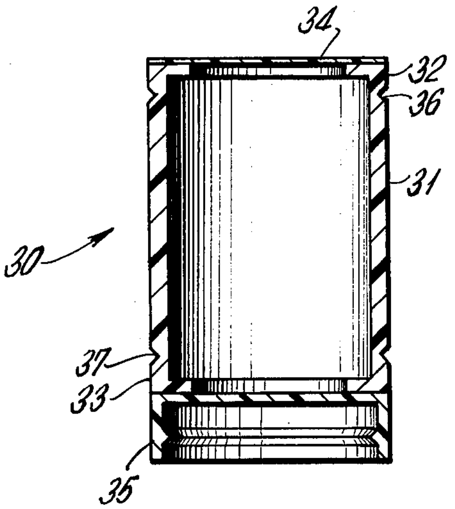
FIG. 5 is a cross-sectional view of an alternative embodiment of a bottom-most cell.

In another embodiment (FIG. 5) of the multicelled container there are no intervening rings and no difference between a bottom cell and connecting cells. Instead, each cell 30 is constructed with a "top" end 32 and a "bottom" end 33. The body portion 31 of the cell is tubular. The "top" end of the cell 30 has its aperture sealed with a plastic membrane 34. An annular indentation (snap groove) 36 is positioned slightly below the top end 32 along with the tubular portion of the cell and a second annular indentation 37 is positioned near the bottom end 33 of the cell. A hard plastic ring 35 is glued on to the bottom end 33 of the cell, the ring having an interior annular bead corresponding with the annular indentation (snap groove) at the neck end of another cell. Successive cells may be thus attached by means of the beads and indentations (snap grooves) to form an air-tight, water-tight and sterile linkage.

Any of these embodiments may include a cell cap to protect the membrane from rupture when the cell is not in use. The cap may be made of plastic molded to fit the neck end of each cell.

An overscabbard made of molded plastic and fitting into the snap grooves along the tubular portion of the cells may be used for further protection when the inter-connected unit of cells is not in use.

Figure 6:
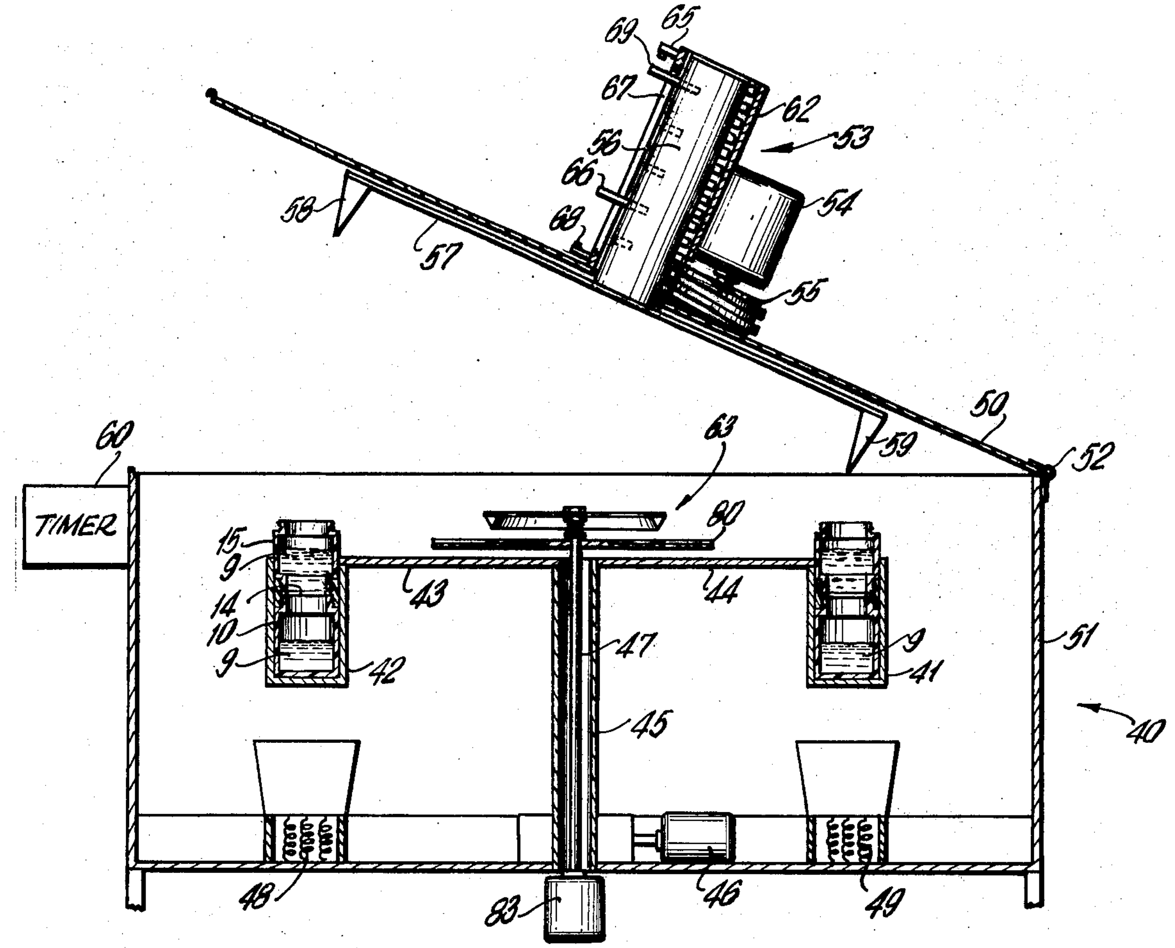
FIG. 6 is a side cross-sectional view of the mixing apparatus of the present invention.

FIG. 6 illustrates the mixer apparatus 40 which is one embodiment of the means for rupturing the membranes of the multi-celled container, motor means for moving said rupturing means, means for agitating and mixing solutions in cells of said container, means for regulating the temperature of said container, means for breaking the micropipette along the scoring line, means for centrifuging the contents of said pipette, and a timing mechanism for regulating each of the rupturing motor, agitator, centrifuge and temperature regulating means. As illustrated, the mixer apparatus 40 contains two holders 41,42 for the multi-celled containers of FIGS. 1, 2 or 5. Each holder 41,42 is attached to an agitator arm 43,44 detachably connected to a vertical tube 45 which is in turn connected to an agitator motor 46. The motor 46 vibrates the tube 45. A vertical rod 47 is positioned within the tube 45 but is not in contact with the tube. The means to centrifuge body fluid samples in the pipettes in which the samples are collected and a pipette breaker to break capillary micropipettes accurately along a scoring line after said pipettes have been centrifuged are connected at the top of rod 47. A centrifuge motor 83 has the rod 47 as its output shaft and rotates the rod 47 within the tube 45 without rotation of the tube 45.

Temperature control means are positioned on the base of apparatus 40. As illustrated, they are electric heating coils 48,49 located directly under the container holders 41,42.

A lid 50 is attached to the frame 51 with a hinge 52. The means 53 for rupturing the membranes separating individual cells of multi-called containers is attached to the lid 50. The motor means for moving the rupturing means includes a rotary motor 54 having an output shaft, and the motor means further includes a gear wheel 55 rotatably mounted on the lid and fixed to the output shaft. The gear wheel 55 meshes with the rack 56 (a rod with gear teeth) which vertically moves in housing 62 attached to lid 50.

The reversible rotary motor fixed on the lid 50 of the mixer apparatus drives the gear wheel 55 in contact with the rack 56, the rack projecting upwardly through the lid and perpendicularly to it. When the motor 54 is put in "forward", the gear rotates in a direction driving the rack downward. When the motor 54 is put in reverse, the gear rotates in a direction driving the rack upward into housing 62.

The rack 56 is perpendicularly attached at its bottom end to a rupture arm 57 which is a flat steel plate with two sharp rupturor blades 58,59 projecting downwards therefrom. The number of rupturor blades 58,59 corresponds to the number of multicelled container holders in the apparatus. For example, there may be two, four or more rupturor blades, depending upon the number of cells used, with one blade being provided for each cell. The blades 58,59 are positioned so that when the lid is closed the blades will be directly above the containers 41,42. Each rupturor blade is of plastic or metal, has a point and has an outside diameter less than the diameter of the neck end of a multicelled container. The blade length is sufficient to rupture the membrane separating the bottom-most cell in a multi-celled container from an adjoining cell.

There are a number of mechanisms which may be used to control the descent of the rack 56, which is a plunger arm. The descent of the rack 56 may be regulated by appendages projecting from it, causing a reverse switch 68 to be depressed at the lowest point of travel of the rack. The reverse switch 68 controls rotary motor 54 and returns the rack 56 upwardly to depress an "off" switch 65 which is fixed to the housing 62. In one embodiment, shown in FIG. 6, holes are drilled in the rack 56 at various distances from the lid 50, corresponding to the various distances which the rack 56 would be required to descend to rupture selected membranes of the multi-celled container. A peg 66 for depressing the "reverse" switch is inserted into the hole corresponding to the distance to be descended by the rack. The peg 66 moves vertically in a vertical slot 67 in the housing 62.

The device operates as follows. The peg 66 is inserted into a hole in the rack 56 at a selected distance from the lid 50, equal to the distance which the rack must descend in order to rupture the selected membrane which separates adjacent cells of a multi-celled container. When the motor 54 is started by the timing mechanism 60, in forward, causing the rack 56 to descend, the descent of the rack 56 continues until the peg 66 reaches the reverse switch 68. When the peg 66 depresses the reverse switch 68, the direction of rotation of motor 54 is reversed, causing the rack 56 to ascend. This ascent continues until the "off" peg 69 located on the rack 56 hits the "off" switch 65 located on the housing 62, depressing the off button and shutting off the plunger motor 54 and preparing it to descend for the next operation.

In an alternative embodiment (not shown) the rack 56 descends against the pressure of a coiled spring. When the peg hits the "reverse" button, the motor stops (but does not reverse) and the gear is disengaged. The rack then rises, driven by the power of the coiled spring.

A timing mechanism is connected by electric wires to the rotary motor 54, agitator motor 46 and heating coils 48,49. In the illustrated embodiment, the timing mechanism 60 is physically attached to the frame 51 of the apparatus.

The rotary motor 45 is wired to the timing mechanism 60. Since the precise rate of descent or ascent of the rack and the rupturing blades attached thereto is a constant governed by the motor and its gear, the rack and attached rupturing means will ascend or descend a precise distance in a precise amount of time.

The timing mechanism is set so that the motor stays "on" for a time corresponding to the distance to be descended by the rupturing means. After this time, a switch is automatically activated, sending the motor into reverse. When the rack has ascended to its original starting place, the motor automatically shuts off.

Alternatively, the rack could be made to descend against the pressure of a coiled spring (not shown). In this embodiment, the timing device regulates only the time required to lower the rack and compress the coil spring, and then it shuts off. When the required descent has been made, the motor shuts off, disengaging the gear, and the rack returns to its starting position by means of the compressed coil spring.

Figure 7:
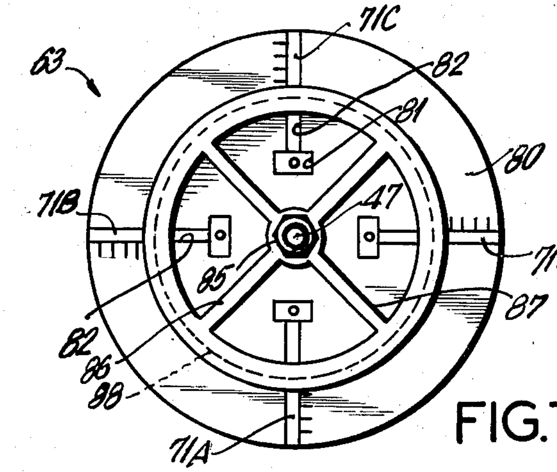
FIG. 7 is a top plan view of the centrifuge and pipette breaker portions of the mixing apparatus.

The centrifuge 63 is shown in FIG. 7. It comprises a flat disc 80, for example, of steel, having a series of indentations 81. As illustrated in FIG. 7, there are four indentations 81 each of which is adapted to hold the bulb 77 and block 75 of a pipette. A channel indentation 82 is directed radially outward from the indentation 81 and is in communication with it. The indentations 82 are used to position the capillary pipettes 71. The plate 80 is fixed, as mentioned before, to the rod 47, which in turn is the output shaft of the centrifuge motor 83. Consequently, when motor 83 operates, it rotates the rod 47 and the centrifuge plate 80. As shown in FIG. 7, pipettes 71A, 71B, 71C and 71D are located in the respective channels 82.

Figure 8:
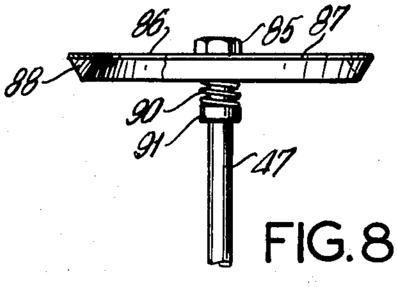
FIG. 8 is a side view of the pipette breaker portion of the mixing apparatus.

An enlarged view of the pipette breaker 61 is shown in FIG. 8. The pipette breaker includes a hub 85 which is rotatably positioned on top of the rod 47. The hub has two or more oppositely directed arms (spokes) 86 and 87 which are attached thereto. A sharp steel blade 88 which is a ring (seen in top or bottom views) is triangular in cross-section and is attached at the ends of the arms 86 and 87. The hub 85 will not rotate with the rod 47 and the hub 85 need not be rotated as the ring blade 88 is positioned so that its point is directly over the score lines 72 on two (or more) of the pipettes. To break the pipettes the hub 85 is vertically depressed, by the technician's finger pressure, and moves downward on the rod 47. The hub moves against the coil spring 90, the coil spring 90 being held up by the flange 91 on the rod 47. The blade 88 will break the pipette at the score lines 72 if there are pipettes within the channels. The coil spring 90 will automatically return the hub 85, along with the blade 88, to its raised position after the finger pressure of the operator is released.

Figure 10:
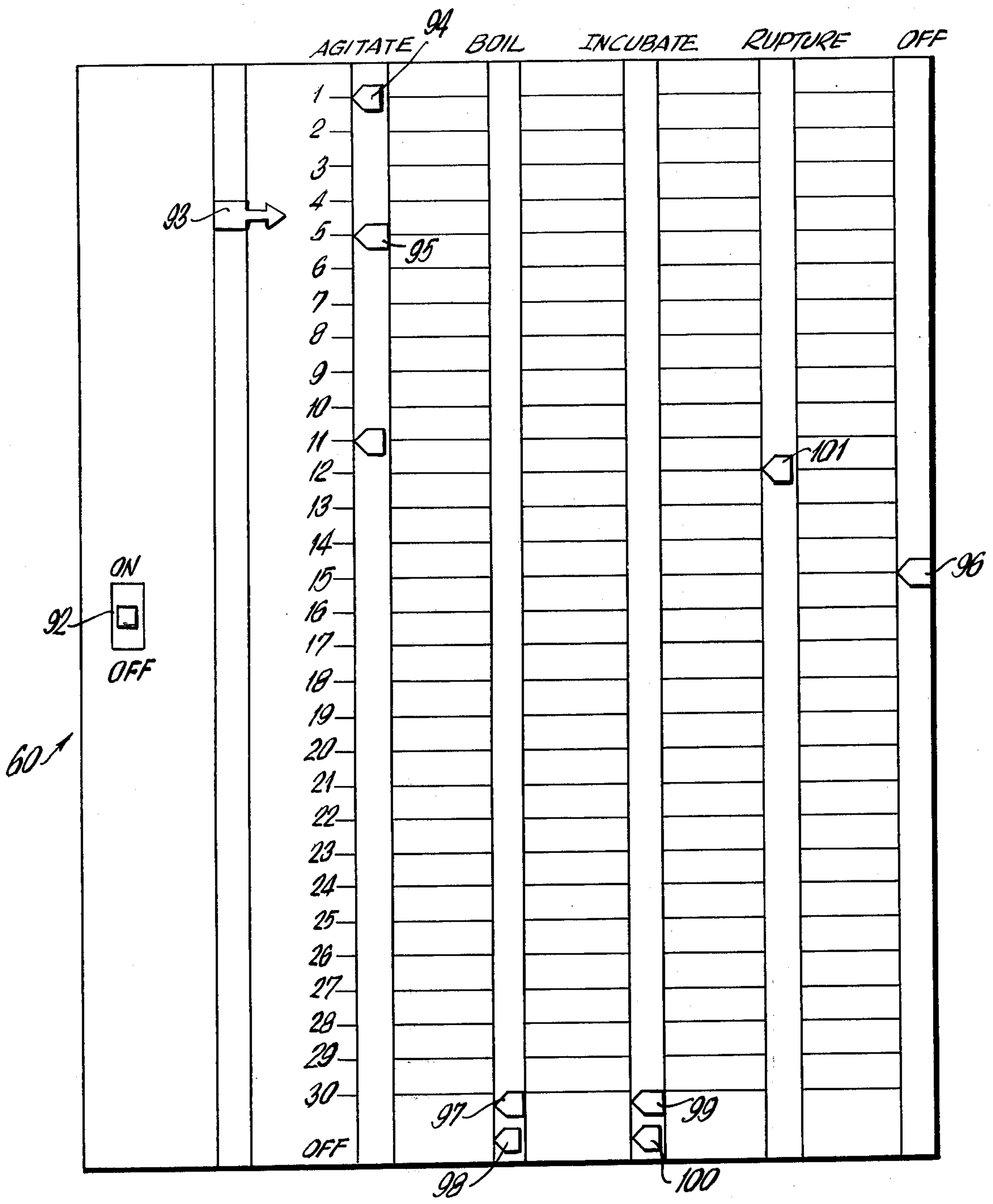
FIG. 10 is an enlarged top plan view of the timing mechanism shown as part of the mixing apparatus in FIG. 5.

The timing mechanism 60, as shown in FIG. 10, consists of a moving time indicator which controls the electric circuitry of the unit by contacting the various contact points, according to the program set by the technician, as it moves along at a constant rate set by the timer motor (not shown). The program is set by placing the movable buttons at the proper time setting.

The technician programs the unit by setting the appropriate buttons for the particular test being performed. When the mixing apparatus is turned on by "on-off" switch 92, the timer indicator, a moving pointer 93, begins to move and the agitator is simultaneously activated by the agitator button 94. For example, a testing utilizing a two-cell container may be set with the "agitate" button 94 at 1 minute and the bottom agitate button 95 at 11 minutes. This setting will agitate the blood-reagent mixture for 10 minutes and then allow it to set for 4 minutes, as determined by the setting of the "off" button 96. At the end of the 10-minute agitator period, the circuitry deactivates the agitator. The rupturing means is operated by setting of button 101. The mixture, after rupture of the membrane by the rupturor blade, falls to the bottom changer and after 3 minutes of agitation the unit is automatically turned off. The technician may then remove the container, after an appropriate rest period, for reading the bottom cell in the spectro-photometer. The boiling and incubation cycles are activated by setting the corresponding start and stop buttons which are 97,98 and 99,100 at the proper numerical setting.

Figure 9:
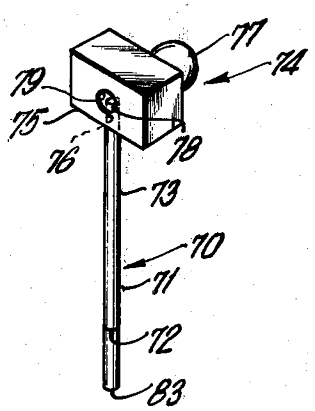
FIG. 9 is a perspective view of the pipette and its attached ejection controlling means.

As shown in FIG. 9, the capillary pipette 70, a micropipette, includes a thin tube 71 having opposing ends open and is made of glass or other suitable material. The pipette is accurately prescored 72 (scratched) by the manufacturer in such a way that when it is filled with body fluid, centrifuged and broken along the scoring line 72, an accurate and predetermined volume of fluid is retained in the upper portion 73 of the pipette 70. Means 74 for regulating the ejection of fluid from the pipette are attached at one end of the pipette.

The pipette 70 has on one of its ends a cubic plastic block 75 whose edge is approximately twice the outside diameter of the micropipette. The block 75 has two holes. The vertical hole 76 is through about ⅔ the length of the block 75 and has the same diameter as the pipette and is closed on the top of the block. The pipette is inserted into the bottom end of the vertical hole 76 and is retained there by friction. A flexible bulb 77 is attached at one end of a horizontal hole 78, for example, by heat-sealing or glue. The horizontal hole 78 is perpendicular to the vertical hole 76 and intersects the vertical hole 76 and goes through the block 75. When blood is drawn into the pipette, the inspection aperture 79 of horizontal hole 78 is left open. The top of the pipette may be viewed through the horizontal hole 78 to ascertain if the pipette is filled with fluid. The technician places his finger over the inspection aperture 79 of the horizontal hole 78 to seal it when the technician squeezes the bulb 77 to aspirate the blood from the pipette into the multi-celled container.

In operation, the process for body fluid analysis using the system of the present invention is as follows. The technician, after obtaining body fluid from the patient, takes one or more pipettes with its bulb attachment and with the inspecting aperture 79 of the pipette uncovered. He places the pipette on a spot of fluid, thus drawing fluid into the pipette by capillary action. He then pushes a piece of putty or clay into the bottom aperture 83 of each pipette to seal the bottom aperture. The pipettes are then centrifuged in the centrifuge 63, the solid matter being forced to the bottom (outer end) and the fluid remaining at the top 73. While in the centrifuge 63, each pipette 70 is broken off at the score line 72, with the pipette breaker 61. Each pipette 70 now has an accurate and predetermined volume of fluid.

In an alternative embodiment (not shown) the pipette may be scored in more than one place, at least one of which places is below the level of solid matter. In this case, after the pipette has been centrifuged, the pipette may be broken off to yield a predetermined volume of solid in the bottom portion of the pipette. This fraction may then be suitably tested.

After the upper portion 73 of the pipette 70 has been broken off, the technician removes the snap cover of the top-most cell, exposing its contents. Preferably, the snap cover is attached to the scabbard. He then closes off the intersecting hole aperture 79, using his finger, and carefully injects the contents of a pipette into the uppermost cell of a multi-celled container by squeezing the flexible bulb 77. He then discards the empty pipette. The technician now closes the lid 50 of the mixer apparatus and activates the timing mechanism 60. According to a preset program, the contents of the cells are agitated, the membranes separating the uppermost cell from its neighbor are ruptured, thus causing the contents of the upper cell to mix with those of the next cell, the resulting mixture agitated, and the mixture heated. Chemical tests may then be performed on the resulting mixture. Since the timing mechanism 60 is attached to the temperature regulating means, the temperature of the solutions in the cells may be varied according to a preset program. If the multi-celled container contains more than two cells, the rupturing-agitating process may be repeated, also according to a preset program.

There are currently about 17 blood chemistries which may be suitable for the mixing apparatus. A few will require boiling, but most will require either incubation or no heating at all. The coils will be activated by the timing mechanism to produce the degree of heat suitable for each test.

The unit will automatically turn off at the conclusion of the cycle and the technician obtains a reading by placing the cell in a colorimeter.

What is claimed is:

1. A mixing apparatus for the automatic testing of body fluids, including:

an accurately prescored capillary pipette for drawing off body fluids, said pipette, when filled with body fluid, centrifuged and broken along said scoring line, having an accurate and predetermined volume of fluid retained in the upper portion of said pipette;

at least one multi-celled liquid-impermeable container having individual cells and a liquid-impermeable membrane sealing between individual cells; a base, means on said base to removably position the container relative to the base; means on said base for rupturing said membrane; motor means on said base for moving said rupturing means to rupture said membrane;

means on said base for agitating and mixing solutions in cells of said container, means on said base for regulating the temperature of said container; means on said base for centrifuging the contents of said pipette before said pipette is broken along said score line; means on said base for accurately and reproducibly breaking said pipette along said score line;

and a timing mechanism connected to and regulating each of the motor means, agitator means and temperature regulation means.

2. A system as in claim 1 wherein a timing mechanism includes a plurality of buttons with each button being associated with and controlling the timing of a function of the apparatus.

3. A system as in claim 1 further including a multi-celled container with at least three cells, each cell being separated from its neighbor by a liquid-impermeable membrane.

4. A process for performing tests upon body fluids comprising the following steps in sequence:

collecting body fluid in an accurately prescored capillary micropipette having opposed open ends and a squeeze bulb fluid ejecting means at one of its ends; stopping an end of said pipette; centrifuging said pipette; breaking off said pipette at its score line to yield an accurate and predetermined volume of fluid retained in said pipette above said score line; transferring said predetermined volume of fluid to the uppermost cell of a multi-celled stacked container with each cell having therein a pre-measured test reagent, and said container having rupturable liquid-impermeable membranes between said cells; said transfer occurring by squeezing said squeeze bulb and thereby injecting said fluid into said uppermost cell; agitating the contents of said container; rupturing the membrane between the uppermost cell and the next cell, thus causing the fluid and reagent in the first cell to mix with the reagent in the next cell; agitating the resulting mixture, and performing a test on the resulting fluid.

* * * * *